United States Patent [19]
Ferreri

[11] 3,948,390
[45] Apr. 6, 1976

[54] LAPAROTOMY SPONGE PACKAGE AND COUNTER

[76] Inventor: John G. Ferreri, 255 Harrell Drive, Spartanburg, S.C. 29301

[22] Filed: Oct. 18, 1974

[21] Appl. No.: 516,018

[52] U.S. Cl. .................. 206/370; 206/72; 128/296; 206/459
[51] Int. Cl.² A61F 13/00; B65D 1/36; B65D 81/36
[58] Field of Search ........... 206/370, 363, 362, 361, 206/72, 73, 438, 464, 45.14, 459; 128/296

[56] References Cited
UNITED STATES PATENTS

| | | | |
|---|---|---|---|
| 1,762,558 | 6/1930 | Mitchell | 206/45.14 |
| 2,659,485 | 11/1953 | Duley et al. | 206/72 |
| 2,710,688 | 6/1955 | Drey | 206/363 |
| 3,138,253 | 6/1964 | Harautuneian | 206/361 |
| 3,481,462 | 12/1969 | Chapel | 206/438 |
| 3,630,202 | 12/1971 | Small | 206/370 |
| 3,856,137 | 12/1974 | Brindley | 206/73 |

Primary Examiner—William T. Dixson, Jr.
Attorney, Agent, or Firm—Cushman, Darby and Cushman

[57] ABSTRACT

A surgical sponge package and counter especially adapted for laparotomy sponges. A bowl-shaped container, having a lip formed around the open end thereof adapted to cooperate with a sheet for sealing the container, has a number of sponges and a sponge-counting card packaged therein. The card has a number of numbered slits formed in one edge thereof, the number of slits corresponding to the number of sponges packaged in the container. The card is placed with the slit edge on top in means formed on the container for supporting the card when it is desired to use the device for sponge counting. Sponges may be directly inserted into the slits in the card, or the slits may receive cords attached to the sponges while the sponges themselves are contained within the container.

5 Claims, 2 Drawing Figures

LAPAROTOMY SPONGE PACKAGE AND COUNTER

BACKGROUND AND SUMMARY OF THE INVENTION

The invention relates to a surgical sponge package and counter especially for laparotomy sponges. As a necessary procedure in all operating rooms, the surgical sponges that are to be used in an operation are removed from their packages, and positioned for use. After the operation is completed, someone must then count each sponge that has been removed from the patient to be sure that the number removed corresponds to the number used — as determined by the number removed from the package and the number not yet used — before the patient can be closed. This is of course a laborious and time-consuming procedure that may result in detriment to the patient if the incision is not closed promptly after the operation is completed or if the count is in error and a sponge is left in the patient.

Various means have been suggested for use in operating rooms to make the sponge-counting procedure easier and more fail safe. U.S. Pat. No. 3,146,944 and 3,367,341 suggest devices that are placed near the site that are used for sponge disposal having electronic and/or mechanical means associated therewith for counting the sponges deposited into the devices. Such devices are cumbersome and expensive, however, and are not entirely fail safe in that if more than one sponge is deposited therein in rapid succession adjacent to each other, as one might have a tendency to do in treating such a device as merely a repository for used sponges, the counter may count only one sponge.

Another device is that shown in U.S. Pat. No. 3,749,237. This device comprises a plurality of interconnected plastic bags, each bag adapted to receive a sponge after use thereof and providing a visual indication of the number of sponges that have been removed and placed therein. While such a means if used properly will provide a clear visual indication of the number of sponges that have been removed, it has the drawbacks of requiring the disposal of a large extra amount of material — the bags — after use, and a means for properly placing the device so that sponges may be easily inserted into the bag openings must be provided otherwise too much time and effort will be required to place the used sponges into the respective bags.

Still another sponge counting device is shown in U.S. Pat. No. 3,481,462. This device contemplates providing a means for both packaging and providing for counting of sponges, and includes a base portion having recesses formed therein, one each for each sponge packaged by the device, and a cover for the base having recesses formed therein complimentary to the recesses formed in the base. While this device is generally satisfactory it has the disadvantages of requiring that the sponges be removed from the package one-by-one, that the sponges must be carefully placed into the counting portion thereof in order to insure that the sponges will be positively located within their respective recesses while still remaining clearly visible, and the cover which forms the counter must be formed separately, thereby requiring two specially formed recessed members that must be produced and disposed of. Also this device is not adapted for use with large sponges such as laparotomy sponges.

According to the teachings of the present invention, all the above-mentioned drawbacks inherent in prior art devices are eliminated. Specifically, the device of the present invention provides a surgical sponge counter and package that is particularly adapted for laparotomy sponges, is relatively inexpensive to make, requires the disposal of relatively little material, positively and clearly locates sponges to be disposed of, and in general provides for ease of counting of sponges removed from a patent to be counted in a fail-safe manner.

According to the present invention, a laparotomy sponge package and counter is provided including a bowl-shaped container having means formed thereon adapted to receive a covering therefor to maintain packaged sponge sterility, and a card disposed within the bowl in addition to the sponges. The card has formed therein a number of slits corresponding to the number of surgical sponges packaged in the bowl-shaped container, and the container has grooves formed in a portion thereof for supporting the card in an upright position. The slits in the card are preferably numbered, each slit also being of a different depth than the preceeding slit.

It is the primary object of this invention to provide a laparotomy sponge packing and counting device that is inexpensive to manufacture, requires the disposal of a relatively small amount of material, and packages the sponges collectively while providing for a clear visual fail safe indication of the number thereof to be disposed. This and other objects of the invention will become clear from an inspection of the detailed description of the drawings and the appended claims.

DETAILED DESCRIPTION OF THE DRAWINGS

Figure 1:
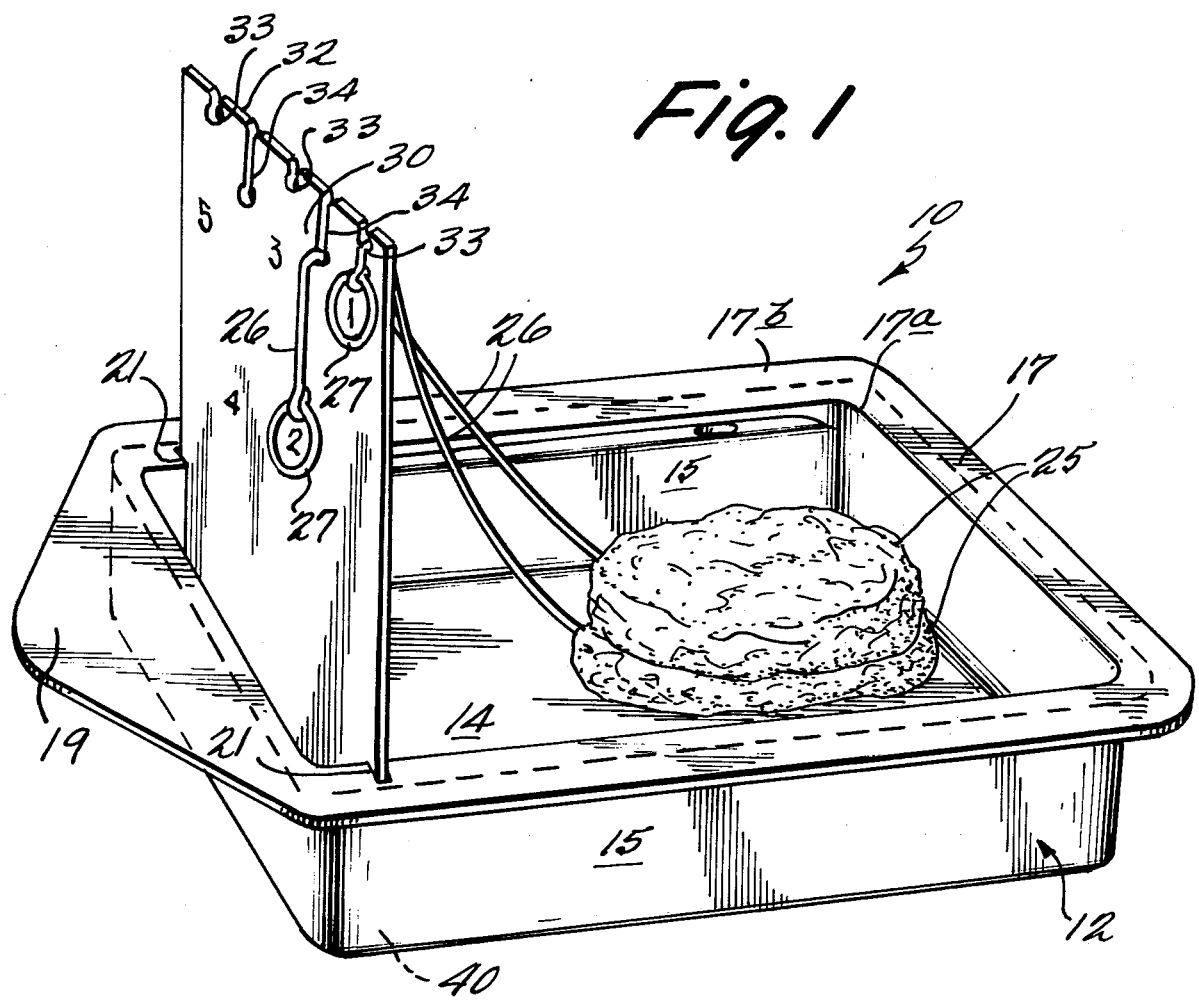
FIG. 1 is a perspective view of device according to the teachings of the present invention shown in the sponge counting position thereof.

A laparotomy sponge packaging device and counter according to the teachings of the present invention is shown generally at 10 in FIG. 1. The complete package according to the invention includes a substantially bowl-shaped container, shown generally at 12, having lip portions 17 formed thereon for cooperation with a means for sealing the open top of the container 12 (such as a sheet of plastic or paper [not shown]), a number of laparotomy sponges 25 disposed within the container 12, and a sponge-counting card 30.

The bowl-shaped container 12 comprises a bottom portion 14 thereof, a plurality of side wall portions 15 enclosing all sides of the bottom portion 14, and a lip portion 17 extending completely around the open top of the container 12. Formed on one end of the lip portion 17 there preferably is an extension 19 adapted to provide for separation of a covering for the open top of the container 12 sealed to the lip portions 17 thereon and the container. The container 12 can be formed of any suitable material, such as relatively lightweight, rigid plastic, and may be one integral structure (including lip portion 17), or may be formed of separate parts operatively affixed together in sealtight relationship. The covering for insuring the sterility of the package may be secured to the lip portion 17 by any suitable means, such as an easily separable adhesive.

The lip portion 17 preferably is formed so that one portion, 17a, thereof extends interiorly of the side wall portions 15, while another portion, 17b, thereof extends outwardly of the side wall portions 15. Formed in the interiorly extending portion 17a are a pair of slits 21, each of sufficient dimension to receive the thickness of a card 30 to be received thereby. Also if desired, other means may be formed with the container 12 for supporting the card 30, such as means 40 forming a groove along the interior walls and bottom of the container 12.

As shown in FIG. 1, the card 30 has a plurality of numbered slits 33, 34 formed in the top edge 32 thereof, one slit for each sponge packaged therewith. preferably, each slit 33 is relatively shallow while adjacent slits 34 are relatively deep. Each slit 33, 34 is dimensioned so that it can receive a string or cord 26 attached to a conventional laparotomy sponge 25. When a cord 26 is received by a slit 33, 34, a ring 27 attached to the bottom thereof is positioned so that it encircles a number corresponding to the respective slit. In this way, a clear visual indication of the number of sponges 25 to disposed of in the container 12 is given.

Although the present invention is not restricted to the dimensions of the container 12 and the laparotomy sponges 25 to be contained therein, preferably the container will be approximately 5 × 9 × 3 inches, the slits 21 being formed in the lip portions 17a along the 9 inch dimension of the container 12. In this way five conventionally sized laparotomy sponges (12 × 12 inches, 18 × 4 inches, 18 × 18 inches, or 8 × 36 inches) and a card 30 may readily be packaged in the container 12. A 6 × 10 inch lidding (such as one of Tyvek) may be placed over the open top of the container and sealed to the lip portions 17 to preserve the sterility thereof after the sponges are sterily packaged.

Figure 2:
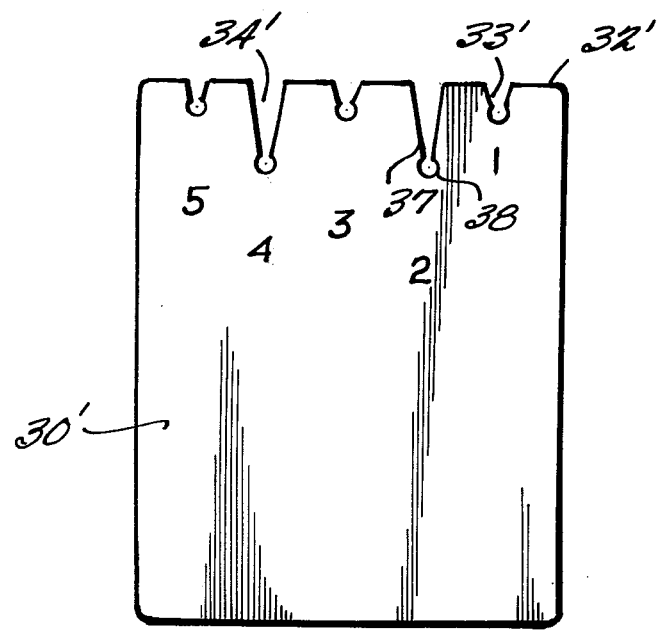
FIG. 2 is a modified form of a sponge-counting card for use with the device shown in FIG. 1.

FIG. 2 shows another embodiment of a card utilizable according to the present invention. The card 30' is adapted for use with surgical sponges not having cords 26 and rings 27 associated therewith — usually smaller sponges than the ringed sponges. The card 30' has a plurality of slits 33', 34' formed in the "top" edge 32' thereof, one slit corresponding to each sponge to be packaged by the container 12. Each slit 33', 34' has sloping side walls 37, and is terminated by an enlarged opening 38. In this way, the card 30' is adapted to receive a complete used sponge to be wedged therein. When using a card such as 30', it is preferable to locate the slits 21 in the lip portions 17a of the container 12 at points closer to the middle of the container than shown in FIG. 1 since it is not required that the plurality of whole sponges rest on the container bottom 14 in the FIG. 2 embodiment. Again, consecutive slits 33', 34' are of different depth, and a number on card 30' is placed adjacent each slit.

The invention shown in FIG. 1 is utilized as follows. When the package 10 is made, a number of sponges 25 are sterily packaged along with a card 30 in the container 12, and sterility of the packaged contents is assured by sealing a lid over the open top of the container 12 in engagement with the lip portion 17 thereof. At extension 19 a separation between lip and covering is provided so that removal of the covering is facilitated.

When it is desired to use the sponges 25 in the package 10, the covering is peeled off, the sponges 25 are taken out and placed in a position for easy access near the site, and the card 30 is removed and placed — with edge 32 thereof on top — in the slits 21. The card 30 has the same number of slits 33, 34 as there are sponges 25 packaged within the container 12, thus providing a fail-safe way of counting the sponges to be disposed of. After each sponge 25 is used, the body of the sponge is placed in the container 12 while the cord 26 thereof is draped over the card 30 through a slit 33 or 34 so that the ring 27 thereof generally surrounds a number placed on the card in cooperation with the respective slit. It is preferable that the slits 33, 34 be filled consecutively so that a clearer visual picture is provided. Once the slits 33, 34 in the card are filled, all of the components may be disposed of. It is apparent that much less material need be disposed of than for prior art devices since only one extra, relatively small element — card 30 — need be disposed of in addition to the normal packaging materials.

The utilization of a package 10 incorporating the card 30' of FIG. 2 is the same as that of the utilization of the FIG. 1 embodiment except that the card 30' is preferably put in slits 21 formed in the container lip portion 17 closer to the middle of the container 12, with the edge 32' thereof on top. The sponges in such an embodiment do not have cords 26 or rings 27 associated therewith, therefore the sponges themselves are inserted into the slits 33', 34' of the card 30', being positively held in place for clear viewing by the sloped wall portions 37 and enlarged termination 38 of the respective slits 33', 34'.

It will thus be seen that a surgical package and counter — one especially adapted for use with laparotomy sponges — has been disclosed that is relatively inexpensive to make, requires the disposal of relatively little material, positively and clearly locates sponges to be disposed of facilitating an easy count thereof, and provides for a fail-safe count of sponges, a disposal position being provided for each sponge packaged Thus the objects of the present invention have been clearly accomplished.

Many modifications are possible; for instance the container 12, slits 21, slits 33, 34, and card-like member 30 may be of any suitable shape or size, and any other suitable means for holding the card-like member 30 upright in container 12 may be provided. While the invention has been herein illustrated in what is presently conceived to be the most practical and preferred embodiments, it will be obvious that many other modifications may be made thereof within the scope of the invention, which scope is not to be limited except by the appended claims.

What is claimed is:

1. A sponge package for packaging and counting sponges comprising
   a. a generally bowl-shaped container having a lip portion formed around the open top thereof,
   b. detachable means for insuring the sterility of sponges packaged in said container for detachably cooperating with said container lip portion,
   c. a number of surgical sponges loosely lying in said container,
   d. a card-like member contained within said container and disposed in a generally flat position and distinct from said sponges said member having an edge thereof having a number of slits formed therein corresponding to the number of sponges disposed in said containers, and
   e. means formed on said container for supporting said card-like member in an upright position extending upwardly from said container past the top thereof, after said means for insuring the sterility of sponges packaged in said container are detached from said container, so that said card-like member may have sponges operatively disposed in the slits formed therein to provide a clear visual indication of the number of sponges disposed therein.

2. A package as recited in claim 1 wherein said means formed on said container for supporting said card-like member comprises a pair of slits formed in opposed portions of said container lip, each of said slits having a width slightly greater than the thickness of the portion of said card-like member to be held thereby.

3. A package as recited in claim 1 wherein consecutive slits formed in an edge of said card-like member are of different length.

4. A package as recited in claim 1 wherein a plurality of indicia are formed on said card-like member, one indicia being formed directly below each of said slits.

5. A package as recited in claim 1 wherein each of said slits formed in said edge of said card-like member has side portions angled toward each other and an enlarged portion at the bottom thereof for holding a sponge therein.

* * * * *